(12) United States Patent
Jorgensen et al.

(10) Patent No.: US 7,001,322 B2
(45) Date of Patent: Feb. 21, 2006

(54) MULTIPLE PROCESSING CHAMBER SET AND USE THEREOF

(75) Inventors: Glen Jorgensen, Marlboro, MA (US); Keith Rosiello, Shrewsbury, MA (US)

(73) Assignee: ZymeQuest, Inc., Beverly, MA (US)

( * ) Notice: Subject to any disclaimer, the term of this patent is extended or adjusted under 35 U.S.C. 154(b) by 0 days.

(21) Appl. No.: 09/970,547

(22) Filed: Oct. 3, 2001

(65) Prior Publication Data

US 2002/0107131 A1    Aug. 8, 2002

Related U.S. Application Data

(60) Provisional application No. 60/237,514, filed on Oct. 4, 2000.

(51) Int. Cl.
  *B04B 7/08* (2006.01)
(52) U.S. Cl. ............... 494/26; 494/29; 494/34; 494/44; 494/45; 92/92
(58) Field of Classification Search ............ 417/387, 417/394, 395; 210/237–241; 494/23, 26–30, 494/45, 44, 31, 33, 34; 222/94; 92/48, 50, 92/90, 92, 93
See application file for complete search history.

(56) References Cited

U.S. PATENT DOCUMENTS

| 599,273 | A | * | 2/1898 | Wahtola ................. 417/244 |
|---|---|---|---|---|
| 988,854 | A | * | 4/1911 | Bixler |
| 1,007,451 | A | * | 10/1911 | Kitts, Jr. |
| 2,000,890 | A | * | 5/1935 | Hueber et al. |
| 2,811,167 | A | * | 10/1957 | Bott ........................... 137/414 |
| 3,503,326 | A | * | 3/1970 | Juhasz et al. |
| 3,561,672 | A | | 2/1971 | Schultz et al. |
| 3,724,497 | A | * | 4/1973 | Federer et al. |
| 4,053,416 | A | * | 10/1977 | Howard et al. |

(Continued)

FOREIGN PATENT DOCUMENTS

| WO | WO 92/00145 | 1/1992 |
|---|---|---|
| WO | WO 98/52629 | 11/1998 |

(Continued)

OTHER PUBLICATIONS

International Search Report for PCT/US01/31125, mailed Jun. 27, 2002.

*Primary Examiner*—David Sorkin
(74) *Attorney, Agent, or Firm*—Foley & Lardner LLP; Michel Morency; John M. Garvey

(57) ABSTRACT

A multiple sample processing apparatus for a continuous flow centrifuge, including a plurality of axially aligned processing chambers and expressor chambers, each chamber comprising an axial opening, in a fixed arrangement, and a plurality of central hubs disposed in the axial openings, the central hubs constructed and arranged to define passages for fluid communication between the chambers and a fluid supply.

8 Claims, 11 Drawing Sheets

U.S. PATENT DOCUMENTS

| | | | |
|---|---|---|---|
| 4,113,173 A | | 9/1978 | Lolachi |
| 4,379,051 A | * | 4/1983 | Hiesinger et al. |
| 4,491,519 A | * | 1/1985 | Kurita |
| 4,610,369 A | * | 9/1986 | Mercier |
| 4,984,970 A | * | 1/1991 | Eickmann |
| 5,019,255 A | * | 5/1991 | Dahlquist et al. |
| 5,547,591 A | * | 8/1996 | Hagihara et al. |
| 5,733,253 A | * | 3/1998 | Headley et al. |
| 6,149,806 A | * | 11/2000 | Baer |
| 6,387,282 B1 | * | 5/2002 | Heckl et al. |
| 2002/0020680 A1 | * | 2/2002 | Jorgensen |
| 2002/0082153 A1 | * | 6/2002 | Jorgensen et al. |

FOREIGN PATENT DOCUMENTS

WO     WO 01/30505 A1 * 5/2001

* cited by examiner

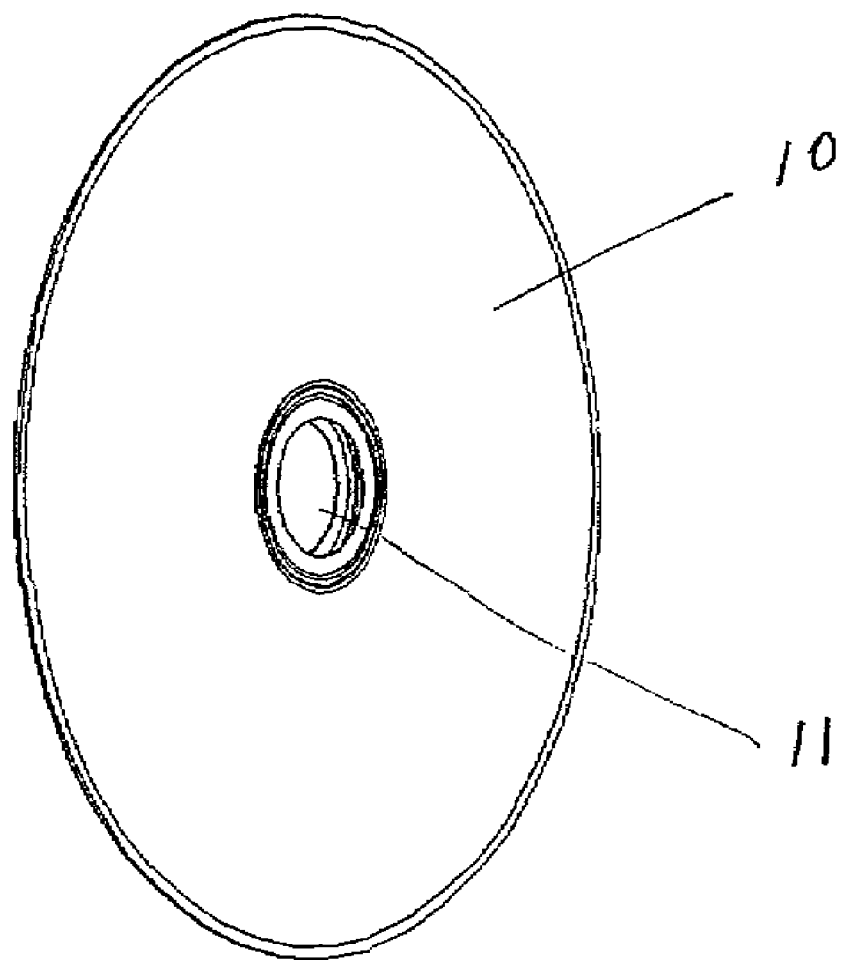
FIGURE 1 EXPRESSOR BAG

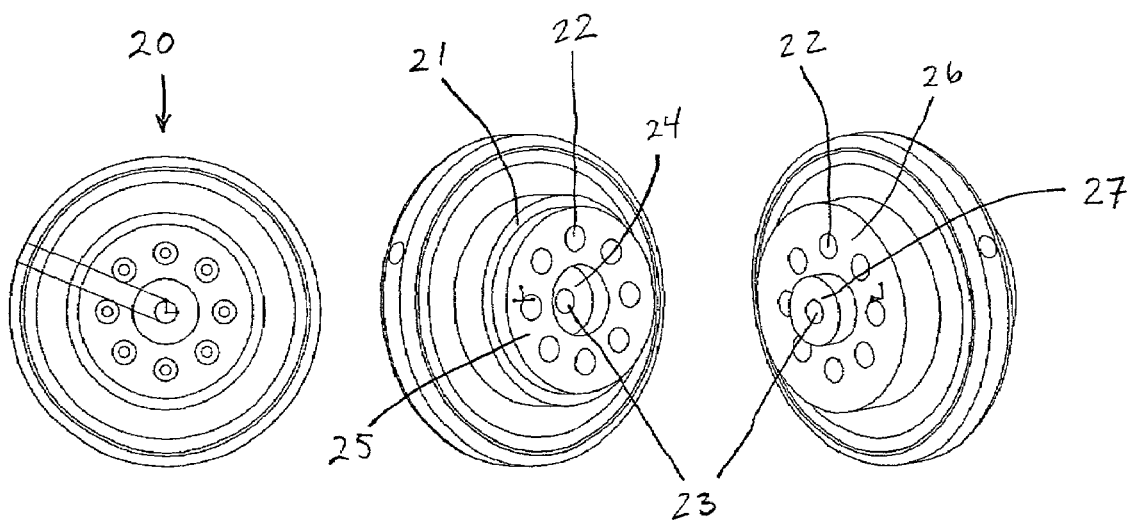
FIGURE 2 EXPRESSOR CENTRAL HUB

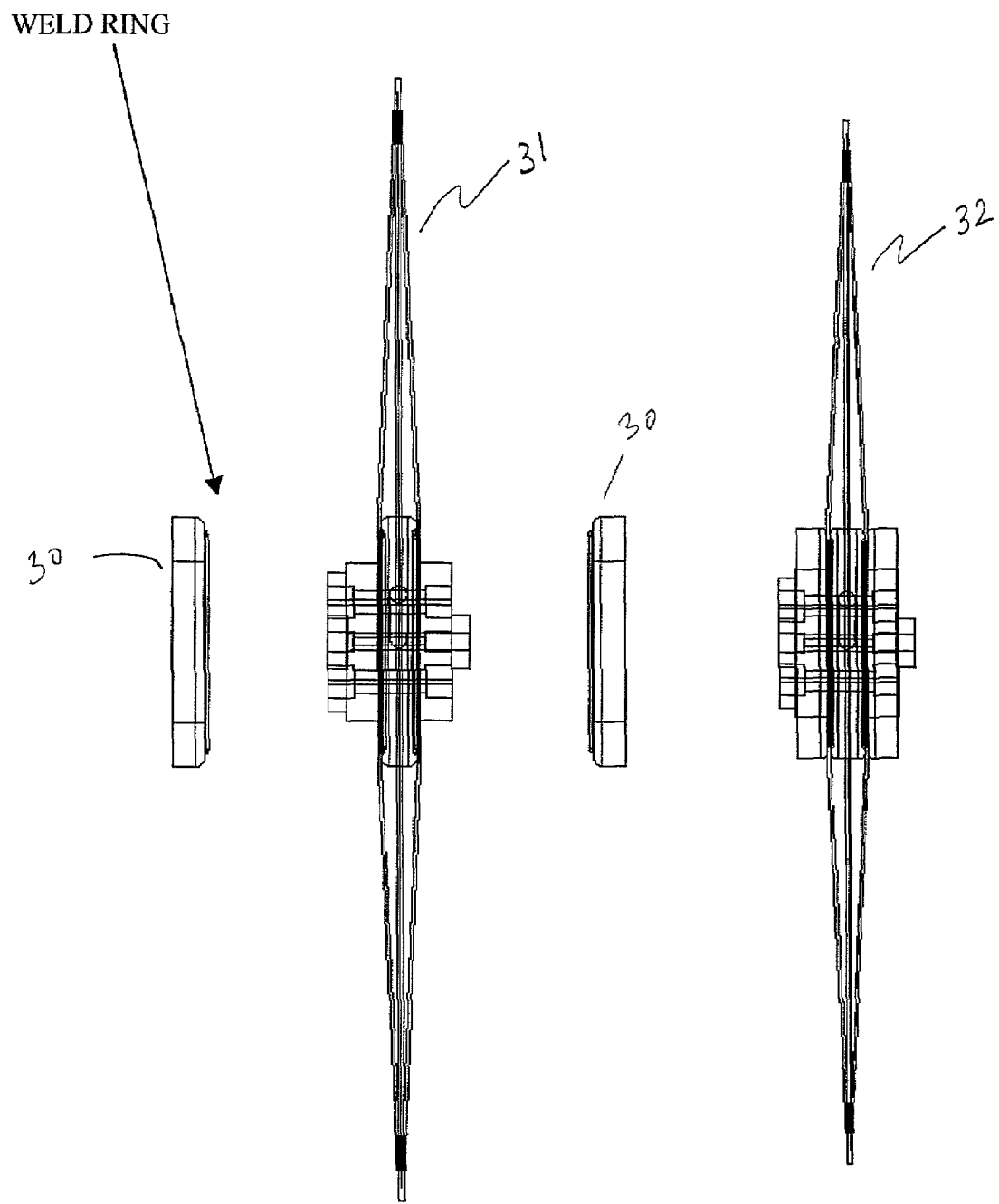
FIGURE 3 EXPRESSOR BAG ASSEMBLY

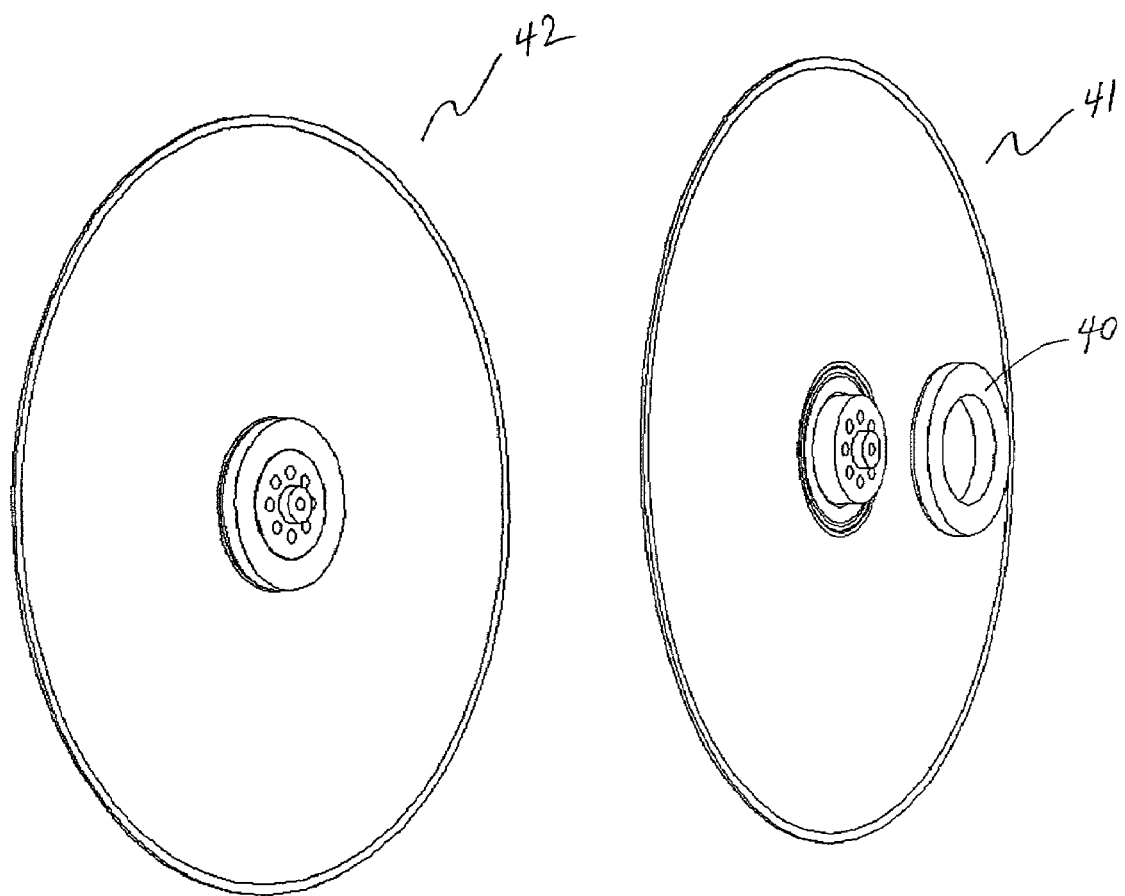
FIGURE 4 EXPRESSOR BAG ASSEMBLY

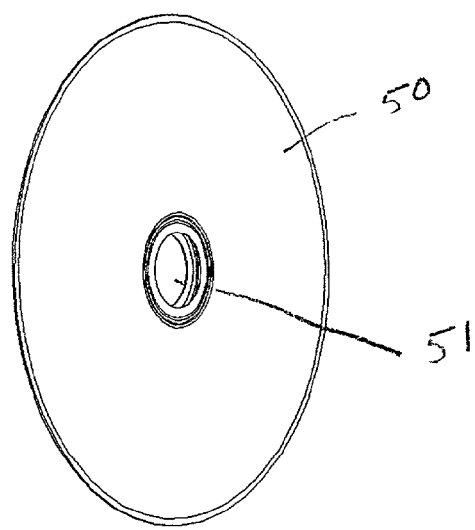
FIGURE 5 PROCESSING BAG
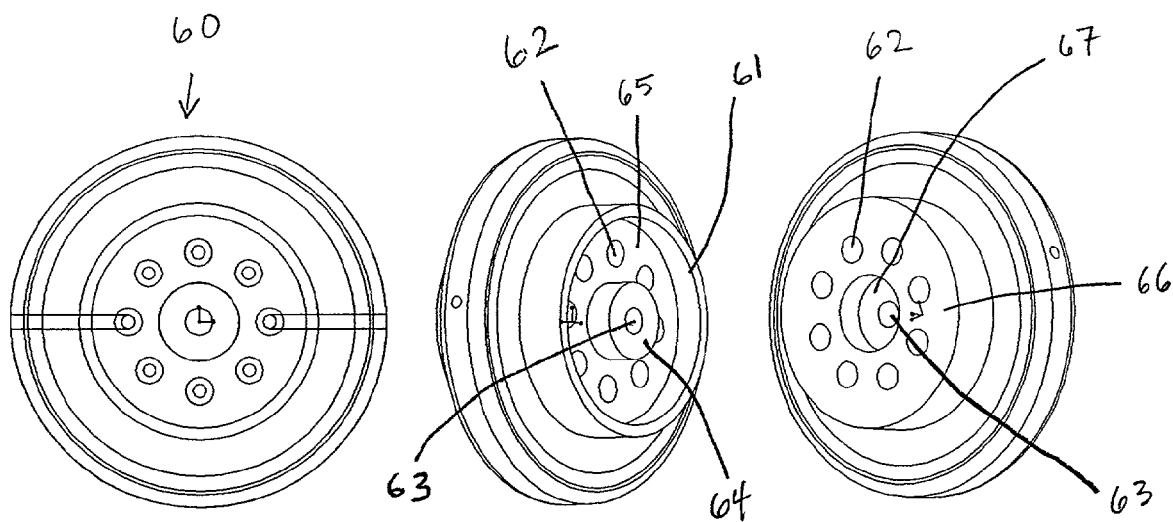
FIGURE 6 PROCESSING CENTRAL HUB

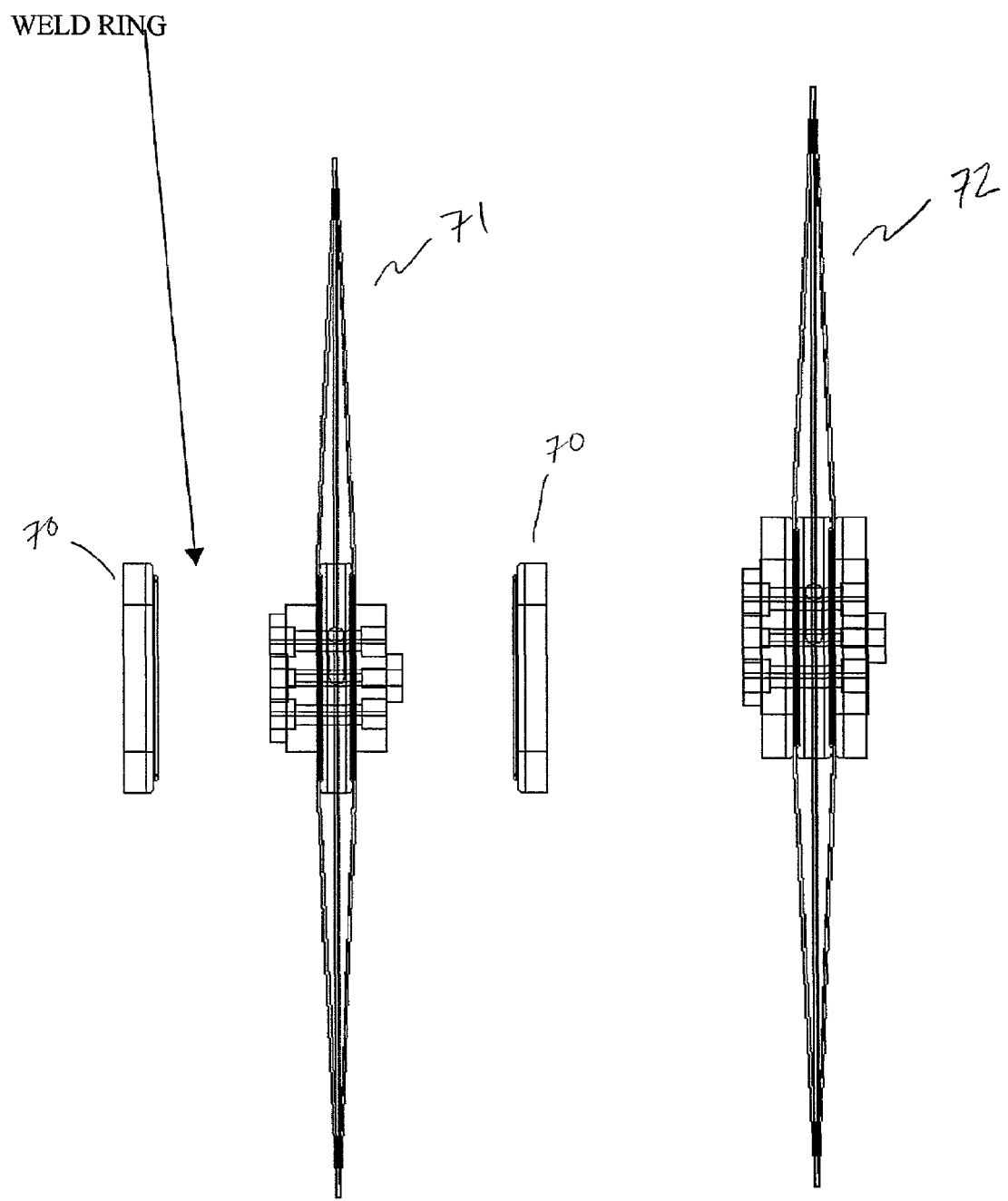
FIGURE 7 PROCESSING BAG ASSEMBLY

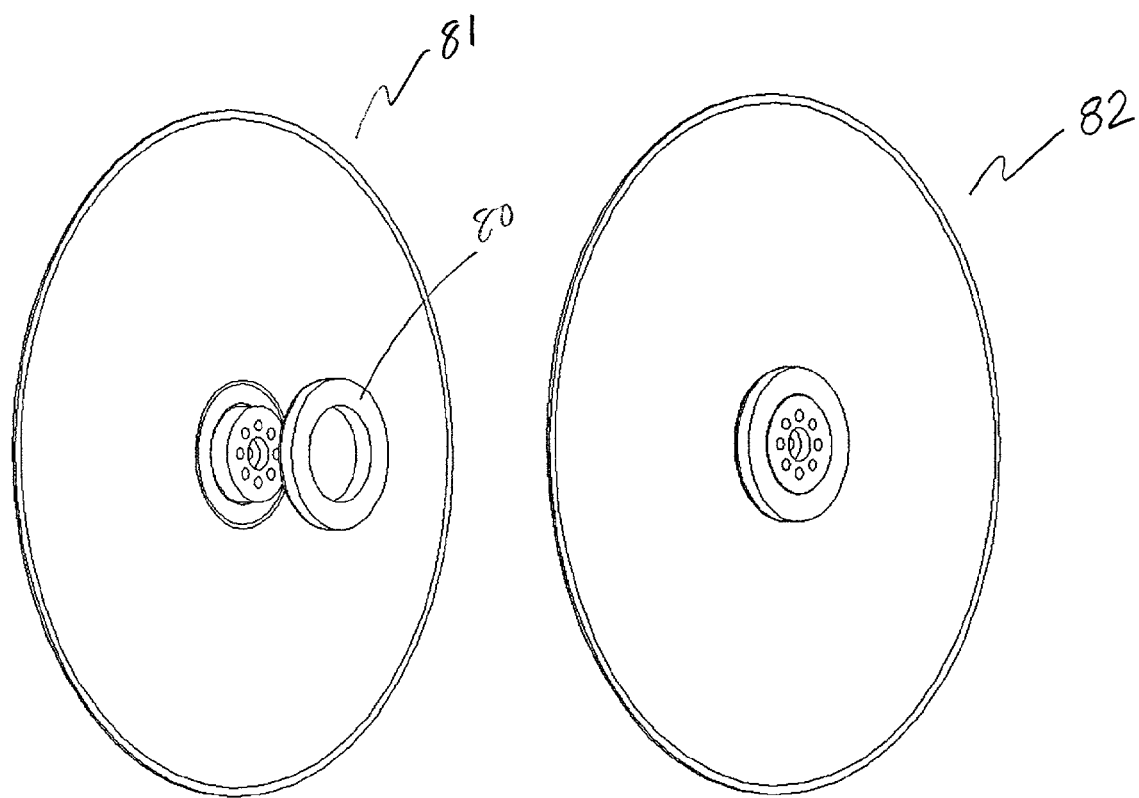
FIGURE 8 PROCESSING BAG ASSEMBLY

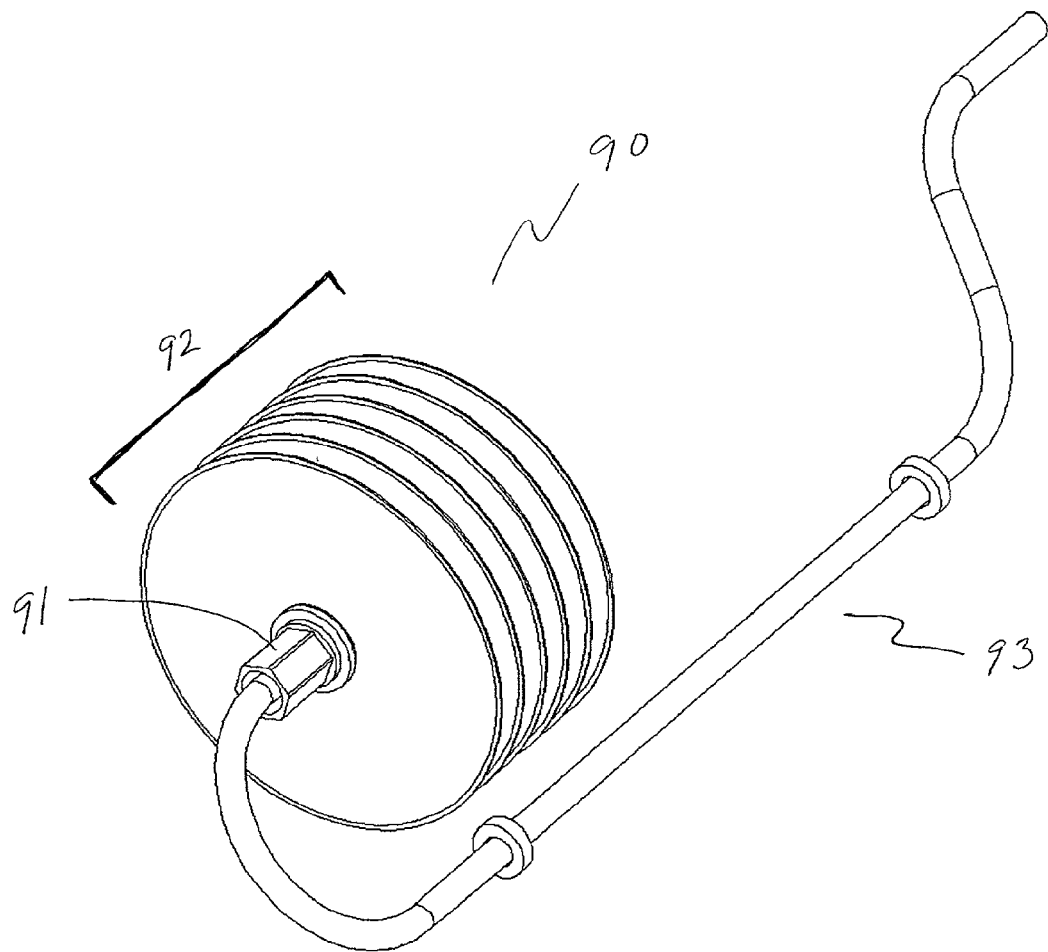
FIGURE 9 BAG SET ASSEMBLY

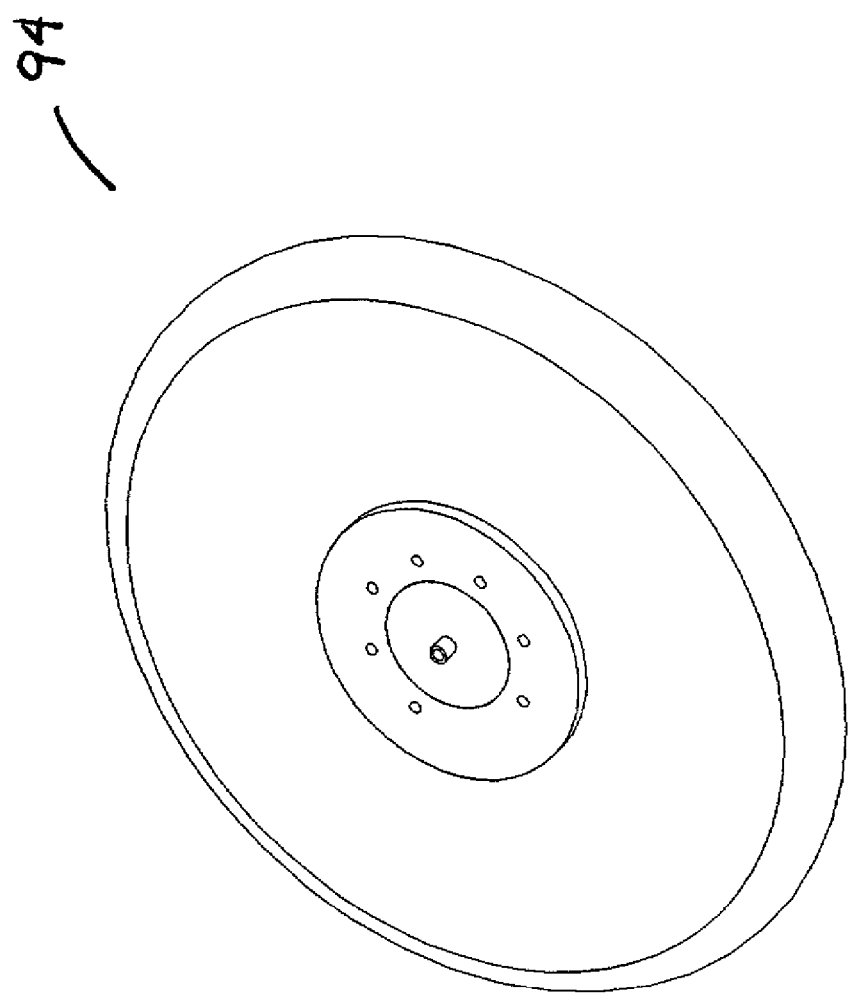

MULTIPLE PROCESSING CHAMBER SET AND USE THEREOF

This application claims benefit under 35 U.S.C. §119(e) of U.S. Provisional Application No. 60/237,514, filed Oct. 4, 2000, the entire disclose of which is herein incorporated by reference.

BACKGROUND OF THE INVENTION

1. Field of the Invention

The invention relates to processing chambers sets for independently and/or simultaneously processing multiple samples of biological cells in a processing device.

2. Background of the Invention

Flexible processing chambers (bags) for processing biological cells in a fixed volume centrifuge, and methods for use of such processing bags, e.g., by centrifugation, are known. For example, PCT patent application PCT/US98/10406 describes a flexible cell processing chamber having a rotating seal to keep the contents of the chamber sterile during processing. Flexible processing chambers advantageously are disposable and thus suitable for single-use sterile applications.

For certain applications, such as blood processing including blood component separation, enzymatic conversion of blood type, and pathogen inactivation of blood components, it is desirable to process multiple units at a time, in a single instrument under the same conditions. Simultaneous processing of multiple units reduces the time and expense required to perform such applications. Present flexible processing chambers do not provide the ability to perform independent simultaneous processing of multiple samples.

One of the difficulties in constructing a multiple processing chamber set is the expression of the contents of the multiple chambers. In any processing protocol, it may be necessary to add and remove processing solutions and chemicals during several steps of the protocol. Thus, it is necessary to be able to efficiently remove the contents of the multiple chambers, usually the supernatant following centrifugation, in a manner that retains the integrity of the multiple chambers and the sterility of the contents contained therein. Accordingly, there is a need for a multiple processing chamber set for biological cell processing in a centrifugal device that maintains sterility of the processed cells and provides for efficient addition and removal of cell samples and processing solutions from multiple chambers simultaneously and/or independently.

SUMMARY OF THE INVENTION

The present invention provides a multiple processing chamber set for biological cell processing in a centrifugal device including processing bags and expression bags. The invention also provides methods for use of such a multiple processing chamber set for biological cell processing in a centrifugal device, including independent and/or simultaneous addition to or expression of contents from the multiple chambers.

According to a first aspect of the invention, multiple sample processing apparatuses for a continuous flow centrifuge are provided. The apparatuses include a plurality of axially aligned processing chambers and expressor chambers, each chamber comprising an axial opening. Preferably the chambers are connected in a fixed arrangement. The apparatuses also include a plurality of central hubs disposed in the axial openings, the central hubs constructed and arranged to define passages for fluid communication between the chambers and a fluid supply. In preferred embodiments, the processing and expressor chambers are constructed and arranged to be flexible and expandable, preferably the chambers are constructed and arranged to releasably contact each other at a circumferential portion of the chambers when the expressor chambers are filled with an expressor fluid. The processor bag and expressor bags may be alternately arranged.

According to a second aspect of the invention, multiple sample processing apparatuses for a continuous flow centrifuge are which include a plurality of axially aligned, processing chambers having expressor chambers incorporated therein. Each chamber also includes an axial opening. Preferably the chambers are connected in a fixed arrangement with the expressor chamber being preferably identically shaped as the processing chamber but slightly smaller to fit within the processing chamber. The apparatuses also include a plurality of central hubs disposed in the axial openings, the central hubs constructed and arranged to define passages for fluid communication between the chambers and a fluid supply. In preferred embodiments, the processing and expressor chambers are constructed and arranged to be flexible and expandable.

In the first aspect and other associated embodiments, the central hubs are constructed and arranged to prevent construction of an apparatus having two adjacent processing chambers. The central hubs of the processing chambers may have a generally disc-like shape with non-complementary sides, such as non-complementary male and female connector shapes. Preferably the central hubs of the expressor bags also are constructed and arranged to prevent construction of an apparatus having two adjacent expressor chambers, in a like fashion. Most preferably the apparatus uses two sets of central hubs, with the shape of one side of the processing chamber central hub being complementary in shape only with one side of the expressor chamber central hub, and the shape of the other (second) side of the processing chamber central hub being complementary in shape only with the other (second) side of the expressor chamber central hub.

In other preferred embodiments, the central hubs are constructed and arranged to define multiple passages for fluid communication, preferably a number of passages that is at least equal to the number of chambers in the apparatus. Thus the central hubs, when connected together, provide continuous unique fluid passages between each chamber and one of more external fluid supplies.

The apparatus also preferably includes a plurality of weld rings disposed on the central hubs, the weld rings being constructed and arranged to permit attachment of processing chambers and expressor chambers, which may be alternately arranged.

In certain embodiments of the invention, the processing chambers and expressor chambers are substantially the same shape, preferably a substantially circular shape, and most preferably having substantially the same diameter. In some embodiments the processing chambers and expressor chambers are constructed from two sheets of flexible material, the two sheets of material sealed at an outer circumference and an inner circumference, although other constructions are also possible and permissible. Preferably, the inner circumference is substantially adjacent the axial opening.

The apparatus in other embodiment also includes a terminal central hub, disposed at a terminus of the plurality of axially aligned alternating processing chambers and expressor chambers. Preferably, the terminal central hub constructed and arranged to terminate fluid flow through the central hub fluid passages.

In additional embodiments, a fluid entry hub is disposed at a fluid entry point of the plurality of axially aligned alternating processing chambers and expressor chambers, and is constructed and arranged to serve as an interface for fluid communication between the plurality of axially aligned alternating processing chambers and expressor chambers and a fluid pathway external to the continuous flow centrifuge. Preferably, the fluid pathway is a multi-lumen tube.

According to another aspect of the invention, an improved continuous flow centrifuge is provided, the improvement including a plurality of axially aligned alternating processing chambers and expressor chambers disposed in a centrifuge bowl, each chamber comprising an axial opening, in a fixed arrangement. In certain preferred embodiments, the plurality of axially aligned alternating chambers is disposed or arranged to provide a horizontal axis of rotation. In other preferred embodiments, each of the plurality of axially aligned alternating chambers is in separate fluid communication through the axial openings with at least one fluid supply container.

According to a further aspect of the invention, a fluid connector for fluid communication between a fluid supply and a plurality of axially aligned centrifuge chambers is provided. The fluid connector includes a multi-lumen disc disposed in an axial opening of the plurality of axially aligned centrifuge chambers, constructed and arranged for fluid communication with a fluid supply and comprising a number of lumens equal or greater than the plurality of axially aligned centrifuge chambers. The fluid connector includes in preferred embodiments at least one lumen constructed and arranged for fluid communication with each of the plurality of axially aligned chambers, thereby forming a plurality of unique fluid communication passages between each of the plurality of axially aligned chambers and the fluid supply. In certain embodiments, the circumference of the disc is substantially circular. In other embodiments, the multi-lumen disc has a first substantially nonplanar surface that defines a shape complementary with a second substantially nonplanar surface of another fluid connector. As above, it is especially preferred that two distinct fluid connectors having shapes that are not self-complementary are provided.

According to still another aspect of the invention, methods for independently and simultaneously processing a plurality of samples in a centrifugal device are provided. The methods include adding a plurality of samples to a plurality of processing chambers of a multiple processing chamber set, centrifuging the plurality of samples. The methods optionally include expressing a plurality of supernatants, the supernatants representing a first portion of the samples formed by the centrifugation of the plurality of samples, and also optionally include expressing a plurality of pellets, the pellets representing a second portion of the samples formed by the centrifugation of the plurality of samples.

According to still another aspect of the invention, a method for independently and simultaneously processing a plurality of samples in a centrifugal device is provided. The device comprises a multiple sample processing apparatus for a continuous flow centrifuge, including a plurality of axially aligned processing chambers and expressor chambers, each chamber comprising an axial opening, in a fixed arrangement, and a plurality of central hubs disposed in the axial openings. The central hubs are constructed and arranged to define passages for fluid communication between the chambers and a fluid supply. The method includes adding a plurality of samples to the plurality of processing chambers, centrifuging the plurality of samples, optionally expressing a plurality of supernatants, including a first portion of the samples formed by the centrifugation of the plurality of samples, and optionally expressing a plurality of pellets comprising a second portion of the samples formed by the centrifugation of the plurality of samples. The supernatants and the pellets are expressed by filling the expressor bags with an expressor fluid.

In certain embodiments, the methods include adding one or more processing fluids to the plurality of samples or pellets. In other embodiments, a portion of one or more of the plurality of samples is expressed independently from the remaining samples. In further embodiments, process fluids are added to one or more of the plurality of samples independently from the remaining samples.

These and other aspects of the invention will be described in connection with the drawings and the detailed description below.

BRIEF DESCRIPTION OF THE DRAWINGS

FIG. 1 depicts an expressor bag having an axial opening.

FIG. 2 depicts three views of an expressor central hub.

FIG. 3 depicts the assembly of an expressor bag by joining two weld rings to an expressor bag and central hub.

FIG. 4 depicts a perspective view of the joining of one weld ring to an expressor bag and central hub.

FIG. 5 depicts a processing bag having an axial opening.

FIG. 6 depicts three views of a processing central hub.

FIG. 7 depicts the assembly of a processing bag by joining two weld rings to a processing bag and central hub.

FIG. 8 depicts a perspective view of the joining of one weld ring to a processing bag and central hub.

FIG. 9 depicts a bag set assembly with six alternating expressor and processing bags 92, a fluid entry hub 91 and a fluid supply tube 93.

FIG. 10 depicts a side view of a bag set of an assembly of a processor bag within an expressor bag embodiment.

DETAILED DESCRIPTION OF THE PREFERRED EMBODIMENTS

Figure 11:
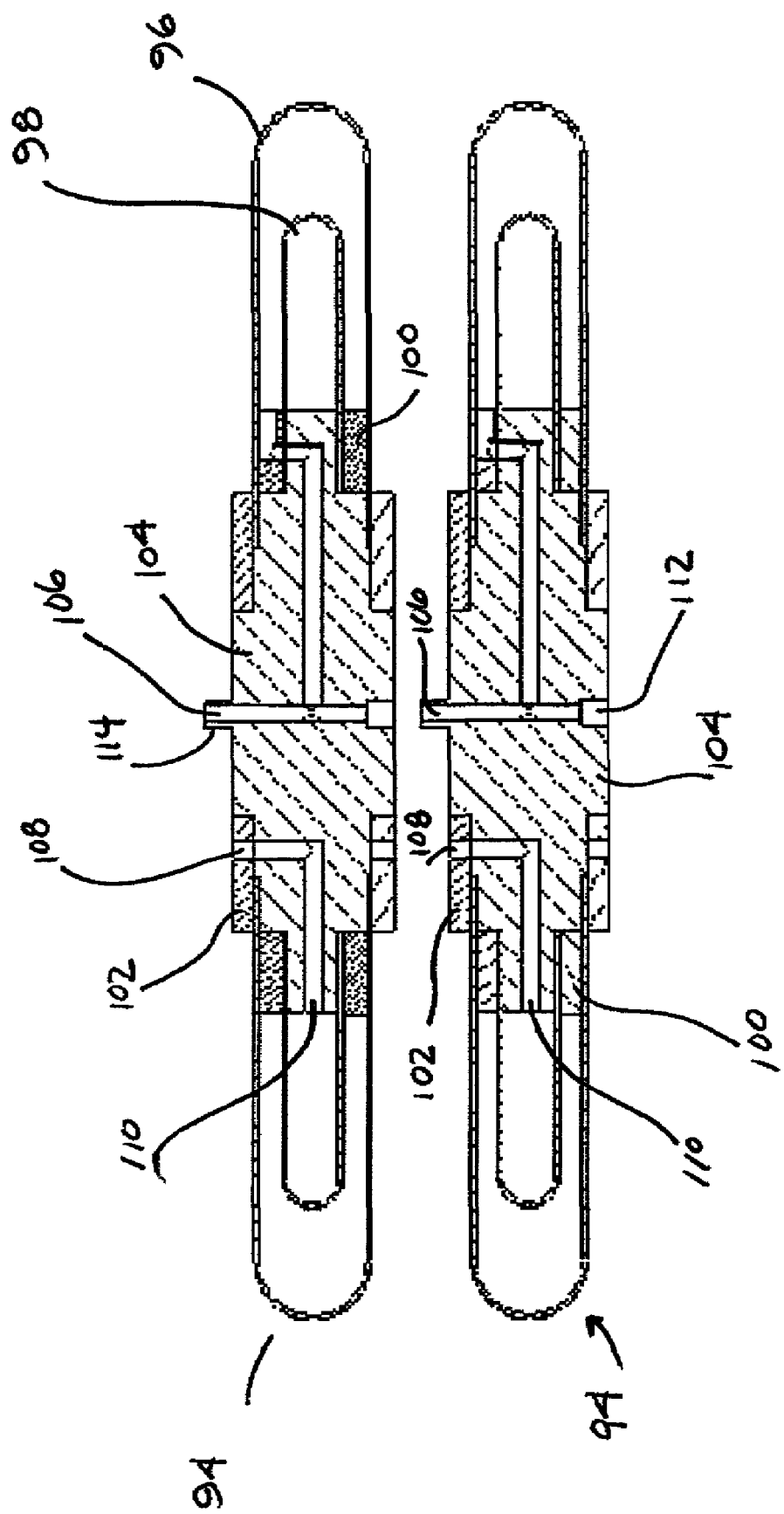
FIG. 11 depicts a cross-sectional side view of an assembly of a processor bag within an expressor bag embodiment.

The invention provides multiple processing chamber sets for processing simultaneously and independently a number of separate samples at one time in a centrifugal cell processing device. The multiple processing chamber sets permit sterile addition and removal of samples (and processed fractions thereof), processing fluids (including enzymes, salts, buffers and other process chemicals), and waste products without the need for rotating seals of any kind. Thus, the multiple processing chamber set represents a portion of a closed system for biological cell processing and includes a number of separate closed containers that can be treated in series or in parallel.

In one embodiment of the present invention, the multiple processing chamber set includes sequentially alternating processing and expressor flexible chambers (also referred to herein as "bags") such that each processing bag is in contact with one or more expressor bags. In one embodiment, the expressor (E) and processing (P) bags are provided in a 1:1 ratio and are alternated in the sequence:

E-P-E-P-E-P-E-P-E.

In another embodiment, the expressor and processing bags are provided in a 2:1 ratio, sequenced to surround each processing bag P with its own set of two expressor bags:

E-P-E-E-P-E-E-P-E-E-P-E.

In each of the foregoing examples, four processing bags P may be provided. The multiple processing chamber sets of the invention can theoretically have any specific number of bags, from two to infinity, to process a like number of samples. Thus, for the application of the multiple processing chamber sets of the invention to blood processing, for example, the number of bags will usually correspond to the number of units or blood to be processed. In such cases, a multiple processing chamber set can be selected that has the appropriate number of processing bags. Alternatively, one or more of the processing bags can optionally be left unfilled or filled with a solution that is not processed if the multiple processing clamber set used contains a greater number of processing bags than the number of samples to be processed.

The optimal number and configuration of bags in the multiple processing chamber set may be constrained by the size and capacity of the centrifugal device, the materials used, or other factors known to one of ordinary skill in the art. Preferably, the multiple processing chamber sets of the invention have between 4 and 16 processing bags, and more preferably have between 8 and 12 processing bags, with appropriate numbers of expressing bags interspersed as described above.

The processing and expressor bags may be placed in the above mentioned alternating sequence with an orientation that places all bags or chambers along a centrally located axis of rotation. Thus the chambers are all axially aligned, i.e., stacked (see FIG. 9, item 92). This axis is defined on each bag by noting the largest bag surface area and finding the center of rotation perpendicular to the largest bag or chamber surface. Preferably the bags are circular in shape, although other shapes may be used.

Each processing or expressor bag is comprised of a flexible compartment, a central hub and weld rings for connecting the flexible compartment to the central hub. As shown in FIGS. 1 and 5 for expressor bags and processing bags, respectively, the bags 10, 50 have an axial aperture 11, 51 where the central hub is joined. The flexible compartment of the processing bag and central hub are constructed of a plastic material that is able to withstand a variety of processing conditions including, but not limited to, changes in temperature, pH, and salt concentrations; application of acceleration, deceleration and centrifugal forces; and application of force from inflation or expansion of the expressor bags. The flexible compartment of the expressor bag is constructed of a plastic material that is able to withstand inflation with expressor fluid or gas. Preferably the flexible compartments of the processing and expressor bags are constructed using a PVC material. Preferably the central hubs and weld rings are constructed using a rigid plastic material.

The central plastic hubs for the processing and expressing chambers are notably different and interlock such that, for proper assembly of multiple processing chamber sets, the alternating sequence of processing and expressing bags in a 1:1 ratio must be maintained. Compare the shapes of the expressor bag central hub depicted in FIG. 2 and the processing bag central hub depicted in FIG. 6. Each of these respective central hubs has a different male-female connection to prevent connection with a like hub. For example, the outer ring 61 that surrounds the male connector 64 of the processing hub will prevent mating with another processing central hub, but fits the outer flange 21 to permit mating with one side of the expressor central hub (middle view). When appropriately mated, matching features of the processing and expressor central hubs will align, e.g., peripheral holes 22, 62, and central holes 23, 63 in all cases; as well as one of the following sets of surfaces: surfaces 24, 64 and 25, 65 or surfaces 26, 66 and 27, 67. Other features of the central hubs provide for proper rotational orientation of the expressor and processing hubs relative to each other to prevent misalignment of peripheral holes 22, 62.

For assembly of multiple processing chamber sets having expressor and processing bags in a 2:1 ratio, a different geometry may be provided for the central plastic hubs that connect the two expressor bags inserted between two processing bags (i.e., the connection underlined: P-E-E-P).

Each of the central hubs contains several independent fluid pathways or passages (e.g., through holes 22, 62 and holes 23, 63 of the central hubs) that interconnect with like passages on subsequent hubs during assembly. The interlocking nature of the hubs forces the fluid pathways to be consistent throughout the assembly such that all fluid pathways maintain independence from one another. Specifically, a single fluid pathway is formed inside the assembled set of hubs that communicates with all the expressing bags or chambers (through holes 23, 63). Further, each processing chamber or bag has a unique and independent fluid pathway through the assembled set of hubs (through holes 22, 62).

The multiple processing chamber set (bag set) is defined as any number of processing bags and associated expressing bags assembled together with central hubs in place. The steps of assembling expressor bags are depicted in FIGS. 3 and 4. FIG. 3 is a side view of the expressor bag assembly, showing the weld rings 30 prior to joining with the expressor bag/central hub assembly 31 (left view) and after joining (right view) to form a fully assembled expressor bag assembly 32. FIG. 4 is a perspective view of one side of the expressor bag assembly, showing the expressor bag/central hub assembly 41 (right view) prior to joining with the weld ring 40, and after the joining (left view) to form a fully assembled expressor bag assembly 42. Likewise, the steps of assembling processing bags are depicted in FIGS. 7 and 8. FIG. 7 is a side view of the processing bag assembly, showing the weld rings 70 prior to joining with the processing bag/central hub assembly 71 (left view) and after joining (right view) to form a fully assembled processing bag assembly 72. FIG. 8 is a perspective view of one side of the processing bag assembly, showing the processing bag/central hub assembly 81 (left view) prior to joining with the weld ring 80, and after the joining (right view) to form a fully assembled processing bag assembly 82.

Once a bag set has been completely assembled by arranging the desired number of processing bag assemblies and expressor bag assemblies, two specific central hubs are mounted, one at each end of the bag set. The central hub furthest from the fluid entry point serves to terminate the fluid pathways, i.e., it is a terminal hub. The central hub closest to the fluid entry point serves as an interface between the bag set and the fluid pathway external to the centrifuge, i.e., it is a fluid entry hub. A completed bag set assembly 90 (i.e., a multiple processing chamber set) is depicted in FIG. 9. Fluid entry hub 91 forms the interface between a multi-lumen tube 93 and the assembled processing/expressor bags 92. The multi-lumen tube preferably includes at least as many lumens as there are processing and expressor bags.

Figure 12:
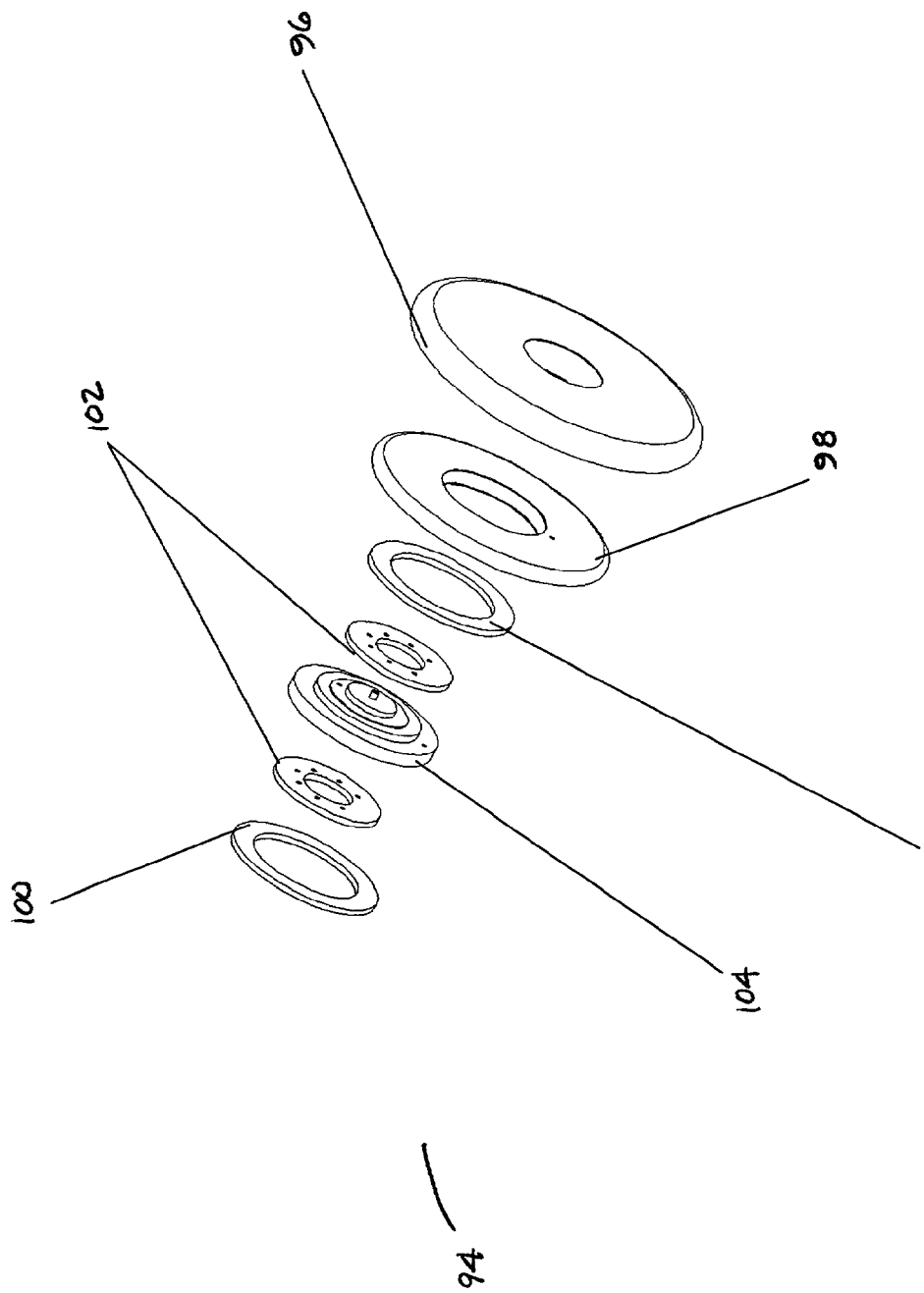
FIG. 12 depicts an exploded perspective view of the assembly of a processor bag within an expressor bag embodiment.

In yet another embodiment, multiple sets of expressor bag and processing bag combinations are assembled in a 1:1 ratio, except that the processor bag is sized smaller than the expressor bag and is placed within the expressor bag, yielding a "bag within a bag" assembly illustrated in FIGS. 10–12.

As shown in these figures, the bag within a bag assembly 94 includes the outer expressor bag 96, an inner processing bag 98, outer weld rings 100, inner weld rings 102 and hub 104. At the center axis, a conduit 106 allows an expressor fluid to be pumped into (and out of) the expressor bag, so that ports 108 allow the supernatant or separated components to flow out of the processing bag via conduit 110.

The hub is designed so that multiple assemblies may be assembled together. Specifically, one side of the hub includes a recess 112 while the other side includes a protruding portion 114 of the conduit 106. Thus, the recess 112 receives a corresponding protruding portion 114 of an adjacent bag within a bag assembly.

The invention further includes methods for independently and simultaneously processing multiple samples in a centrifugal device. In particular, the invention provides for the use of a multiple processing chamber set in the processing of biological cells according to defined protocols in a cell processing device. The methods are useful for cell washing, blood component separation, blood component processing, including enzymatic conversion of the blood type of red blood cells (e.g., types A, B or AB to type O red blood cells), pathogen inactivation of biological fluids or cells, and the like. The methods utilize a defined processing protocol that involves adding one or more samples to the processing bags of the multiple processing chamber set, optionally centrifuging the samples, optionally expressing a supernatant formed by the centrifugation, adding one or more process chemicals or fluids, etc. Processing protocols are known to those of skill in the art, and an exemplary method follows.

The method of separating or processing samples can be defined in several steps subsequent to the assembly of the bag set. The initial step involves mounting the bag set into a continuous fixed volume centrifuge. The fluid (e.g., blood) to be separated or processed is drained, pumped or otherwise loaded into the processing chambers or bags and the components separated using centrifugation. For expression of supernatant fluid or separated components, the centrifuge is slowed to expression speed while the component interface is maintained. At this point, expressor fluid (see, e.g., PCT patent application PCT/US98/10406) is delivered into the expressor bags, preferably via a metered pump. As the expressor fluid fills the expressing bags, the overall volume of the centrifuge compartment available to the processing bags is reduced proportionally. Thus, because of the fixed centrifuge volume, as the expressor fluid fills the expressing bags, the contents of the processing bag are emptied or expressed. Further, the contents of the processing bags are expressed preferentially from least dense to most dense due to the centrifugation and the fact that expressor fluid is denser that the densest component held within the processing chamber.

The expressor fluid may include two fluid components that, when mixed together, create a fluid that is heavier than the heaviest component of the biological sample. For example, if the biological sample is blood, the two fluid components mixed create a fluid heavier than the red blood cell component (i.e., the heaviest component) of blood, so that all the components of the blood (e.g., red blood cells, white blood cells, palettes) may be separated and removed from the processing bags.

However, if only certain components of the biological sample are required to be separated, then the expressor fluid may not be required to be heavier than the heaviest component of the sample. For example, if red blood cells are the only component that required separation from a blood sample, then an expressor fluid comprised substantially of air may be used.

Thus under centrifugal force the expressor fluid will fill the expressor bags from the outermost radial portion inward to the innermost radial portion as disclosed in PCT patent application PCT/US98/10406. Finally, as the expressor bags fill from the outermost radial portion inward, the reduced volume within the processing bags causes the fluid at the innermost radial portion of the processing bags to be expressed. Following expression, the expressor fluid can be removed, if desired, from the expressor bags by the application of a vacuum to the expressor bag supply line(s), the use of expressor fluid also permits the adjustment of the volume of the processing bags as needed, for example, for different protocols or for different steps of a single protocol. One skilled in the art will appreciate that if air is used as the expressor fluid, it may be removed in a much shorter period of time than the usual heavier expressor fluids used to separate more components of the sample.

Subsequent protocol steps may include washing of cells after supernatants are expressed. Wash fluids and/or processing fluids, etc., are introduced into the processing bags as the sample was, and incubated with the sample. The processing bags may be agitated is desired by reversing the direction of the centrifuge drive, by running the centrifuge intermittently, and so on.

Each of the foregoing patents, patent applications and references is hereby incorporated by reference.

While the invention has been described with respect to certain embodiments, it should be appreciated that many modifications and changes may be made by those of ordinary skill in the art without departing from the spirit of the invention. It is intended that such modification, changes and equivalents fall within the scope of the following claims.

What is claimed is:

1. A multiple sample processing apparatus for a continuous flow centrifuge, comprising a plurality of axially aligned processing chambers and expressor chambers, each processing chamber arranged within a corresponding expressor chamber and including an axial opening housing a central hub, wherein a respective central hub of a respective chamber includes at least one first dedicated passageway aligned substantially parallel to a central axis of the hub dedicated for fluid communication with a first chamber and at least one second dedicated passageway aligned substantially parallel to the central axis of the hub for fluid communication with a second chamber.

2. The apparatus of claim 1, wherein the processing and expressor chambers are constructed and arranged to be flexible and expandable.

3. The apparatus of claim 1, wherein the central hubs are constructed and arranged to define multiple passages for fluid communication.

4. The apparatus of claim 3, wherein the central hubs comprise a number of passages for fluid communication that is at least equal to the number of chambers in the apparatus.

5. The apparatus of claim 1, wherein the processing chambers and expressor chambers are substantially the same shape.

6. The apparatus of claim 5, wherein the processing chambers and expressor chambers are substantially circular.

7. The apparatus of claim 1, wherein the processing chambers are smaller than the expressor chambers.

8. The apparatus of claim 7, wherein the processing chambers have a smaller diameter than the expressor chambers.

* * * * *